United States Patent
Musyl et al.

(10) Patent No.: US 10,376,248 B2
(45) Date of Patent: Aug. 13, 2019

(54) MAMMAL AND FISH BIOPSY DART

(71) Applicant: TISSUEGRAB BIOPSY SYSTEMS LLC, Honolulu, HI (US)

(72) Inventors: Michael K. Musyl, Honolulu, HI (US); Lianne McNaughton, Saskatoon (CA)

(73) Assignee: TISSUEGRAB BIOPSY SYSTEMS LLC, Honolulu, HI (US)

( * ) Notice: Subject to any disclaimer, the term of this patent is extended or adjusted under 35 U.S.C. 154(b) by 347 days.

(21) Appl. No.: 15/211,526

(22) Filed: Jul. 15, 2016

(65) Prior Publication Data
US 2018/0014818 A1 Jan. 18, 2018

(51) Int. Cl.
*A61B 5/00* (2006.01)
*A61B 10/02* (2006.01)
*F42B 6/00* (2006.01)

(52) U.S. Cl.
CPC .......... *A61B 10/0266* (2013.01); *F42B 6/003* (2013.01); *A61B 2503/40* (2013.01)

(58) Field of Classification Search
CPC . A61B 10/02; A61B 10/0233; A61B 10/0266; A61B 10/0275; A61B 2503/40; F42B 6/003
USPC .......................................... 600/567; 606/184
See application file for complete search history.

(56) References Cited

U.S. PATENT DOCUMENTS

| | | | | |
|---|---|---|---|---|
| 5,827,199 A | * | 10/1998 | Alexander | A61B 10/00 600/564 |
| 5,895,403 A | * | 4/1999 | Collinsworth | A61B 17/32053 606/184 |
| 6,110,128 A | * | 8/2000 | Andelin | A61B 10/025 600/566 |
| 7,722,548 B2 | | 5/2010 | Cervi | |
| 2012/0197157 A1 | | 8/2012 | Ryan et al. | |

OTHER PUBLICATIONS

Floy Tag brochure, Floy Tag, 4616 Union Bay Place NE, Seattle, WA 98105 US, Mar. 1998, website www.FloyTag.com.
The PAXARMS Biopsy System for Small Cetaceans, pp. 1-4, retrieved from the internet on Jul. 8, 2013.
Murdock University Animal Ethics Committee, SOP (0100-03): Wildlife (Marine)—Remote biopsy sampling of cetaceans, Jul. 2009, pp. 1-7.

(Continued)

*Primary Examiner* — Max F Hindenburg
(74) *Attorney, Agent, or Firm* — Greenberg Traurig, LLP

(57) ABSTRACT

A dart for use in gathering a tissue sample from an animal is disclosed. The dart has an adapter base for fastening to an elongated dart delivery shaft. The adapter base has a distal threaded end. A dart tip is threaded onto the adapter base. The dart tip has a sharpened tubular end portion for entering through skin of an animal and a cylindrical chamber portion for receiving and holding at least part of a tissue sample. The chamber portion has a proximal portion adapted to be removably fastened to the distal threaded end of the adapter base and a distal portion merging with the sharpened tubular end portion, wherein the dart tip is configured to hold and retain the tissue sample received within the chamber portion while the dart tip is withdrawn from the animal.

20 Claims, 3 Drawing Sheets

(56) References Cited

OTHER PUBLICATIONS

Browning, N. E., et al. "Fine-scale population structure of estuarine bottlenose dolphins (*Tursiops truncatus*) assessed using stable isotope ratios and fatty acid signature analyses." *Marine biology* 161(6) (2014): 1307-1317.

Cunha, H. A., et al. "A new skin biopsy system for use with small cetaceans," LAJAM 8(1-2):183-186, Dec. 2010.

Karesh, W. B., et al., "A Remote Method for Obtaining Skin Biopsy Samples," *Conservation Biology*, vol. 1, No. 3. Oct. 1987, pp. 261-262.

Kiszka, J. J., et al., "Individual and group behavioural reactions of small delphinids to remote biopsy sampling," *Animal Welfare* (2010) pp. 411-417.

Krutzen, M., et al., "A biopsy system for small cetaceans: darting success and wound healing in *tursiops* spp.," Marine Mammal Science, 18(4):863-878 (Oct. 2002).

Nishiwaki S., "Performance of biopsy skin sampling for minke whales during the JARPN and JARPA surveys using ICR air gun," Paper SC/52/O5, presented to the IWC Scientific Committee, Jun. 2000, pp. 1-8.

Petersen, S. D., et al., "Preliminary investigation of genetic capture-mark-recapture to census bowhead whales (*Balaena mysticetus*) in Nunavut, Canada," Research Document 2014/017, Central Arctic Region, Fisheries and Oceans Canada, Canadian Science Advisory Secretariat, 200 Kent Street, Ottawa, ON K1A 0E6, May 2014, pp. 1-9.

Ryan, Conor, "Fourth IWDG Humpback Whale Research Expedition: Cape Verde 2012," pp. 1-19, 2012.

Wenzel, F., et al., "Northeast Fisheries Science Center Reference Document 10-11: Northeast Fisheries Science Center Cetacean Biopsy Training Manual," Jun. 2010, US Dept. of Commerce, NOAA, National Marine Fisheries Service, Northeast Fisheries Science Center, Woods Hole, Massachusetts, pp. 1-18.

Willis, P. M., et al., "Natural hybridization between Dall's porpoises (*Phocoenoides dalli*) and harbor porpoises (*Phocoena phocoena*)," *Can. J. Zool.* 82:828-834 (2004).

Worthy, G. A. J., et al., "Fine scale feeding habits of bottlenose dolphins in the western Florida panhandle as assessed by stable isotope signature analysis," The Society for Marine Mammalogy, $19^{th}$ Biennial Conference, Tampa, Florida Nov. 26-Dec. 2, 2011, 1 page.

\* cited by examiner

MAMMAL AND FISH BIOPSY DART

BACKGROUND OF THE DISCLOSURE

This disclosure relates generally to biological sample (i.e., tissue) collection devices and more particularly to a device for collection of tissue samples from live marine mammals and fishes.

Field biologists collect biological tissue samples (or "biopsy" samples) from marine mammals, marine and freshwater fishes, and sharks for a variety of purposes, for example; to study their physiology, reproductive status, health and morbidity, and to delimit spawning sites, stock boundaries, levels of gene flow, migration corridors and effective population size (among other things). It is preferable to collect tissue samples in-situ or, over-the-side of the vessel, as it minimizes stress to the animals that can be incurred by bringing these animals on-board the vessel to sample their biological tissues. For fishes and sharks, time out of water is a critical factor to minimize stress, injury and mortality. In other words, scientific sampling should not be a contributing factor to the morbidity of the subject; particularly if they are endangered species.

In situations where animals are brought on-board vessels; presently, there are no standardized sampling devices used to collect biopsy samples nor is there a recommended volume or mass of tissue to acquire. A common method for onboard sampling involves collecting samples using a sharp knife; a technique that can needlessly injure the animal (and the researcher). Note that certain shark species (e.g., blue shark *Prionace glauca* and Greenland shark *Somniosus microcephalus*) will pose challenges to any biopsy sampling device or instrument, particularly during mating season.

Current technologies and biopsy sampling devices and instruments for human and veterinary use are not reliable and effective at collecting the required volume/mass of tissue during sampling for many marine mammals, fishes and sharks. Failure to collect an adequate tissue sample on the first attempt requires additional attempts. Repetitive sampling of living tissue can needlessly injure the animals and lead to higher morbidity. Often, a 'sample' can be collected but it will contain insufficient amounts of tissue for the sample to be viable or it may contain non-target material (e.g., mucus, scales). Moreover, another common occurrence is when the animal subject has already been released but the researcher learns later that the sample is insufficient and therefore not useful, and the animal has been needlessly injured. For rarely encountered and/or endangered species, these wasted opportunities represent a tremendous sacrifice of information and resources. If the animal has not been released, then additional attempts to take a sample may be required; again needlessly subjecting the animal to prolonged stress, trauma, injury and potentially mortality.

Therefore there is a need for a minimally invasive biopsy sampling device that will circumvent needless injury to subjects, significantly eliminate or reduce repetitive sampling attempts and will maximize sampling opportunities and therefore the cost-benefit of these sampling programs.

SUMMARY OF THE DISCLOSURE

A biopsy dart in accordance with the present disclosure meets these needs. The biopsy dart is a minimally invasive biopsy sampling device used to collect biological tissue samples (e.g., blood, blubber, muscle, skin) from marine mammals in particular (i.e, cetaceans and delphinids), elasmobranchs (sharks) as well as salt and freshwater teleosts (fishes). The device reported herein is also referred to as a "biopsy device, biopsy instrument, biopsy needle, biopsy tip, sampling device, sampling tip, sampling instrument, sampling needle, trocar, trochanter" and by various combinations of these keywords and descriptors.

One embodiment of a device in accordance with the present disclosure includes an adapter base for fastening to an elongated dart delivery shaft or striking device such as a pneumatic gun projectile, a dart tip having a sharpened tubular end portion for entering through skin of an animal and a chamber portion for collecting and holding a tissue sample, wherein the chamber portion has a proximal portion adapted to be fastened to the adapter base and a distal portion merging with the tubular end portion, and one or more barbs formed in the chamber portion for preventing withdrawal of the tissue sample through the sharpened tubular end portion while the dart tip is withdrawn from the animal. Preferably the one or more barbs project inward and toward the adapter base. The sharpened tubular end portion has two V shaped end points. These end points may be at the same axial location or may be at different axial locations. In one embodiment the tubular end portion terminates in two V shaped cuts each at an angle of about 30° to a longitudinal axis through the dart. The tubular end portion may be externally tapered or straight.

A dart for use in gathering a tissue sample from an animal in accordance with an exemplary embodiment includes a generally cylindrical adapter base for fastening to a dart delivery shaft, the adapter base having a distal threaded end, a dart tip having a sharpened tubular end portion for entering through skin of an animal and a chamber portion for collecting and holding a tissue sample. Preferably the chamber portion has a proximal portion adapted to be fastened to the distal threaded end of the adapter base and a distal portion merging with the sharpened tubular end portion. A plurality of barbs are formed in the chamber portion for preventing withdrawal of the tissue sample through the sharpened tubular end portion while the dart tip is withdrawn from the animal.

An embodiment of the dart in accordance with the present disclosure may include the sharpened tubular end portion having two V shaped ends that are at different angles. An embodiment may include from two to six barbs spaced symmetrically around a collar of the chamber portion. The tubular end portion preferably can terminate in two V shaped cuts at least one of which is at an angle of about 30° to a longitudinal axis through the dart. The distal portion of the chamber may be cylindrical or may optionally be externally tapered. The tubular end portion may terminate in two V shaped cuts at least one of which is at an angle of about 30° to a longitudinal axis through the dart.

An exemplary dart for use in gathering a tissue sample from an animal in accordance with the present disclosure may include an adapter base for fastening to an elongated dart delivery shaft or striking device such as a pneumatic gun projectile. The adapter base has a distal threaded end. The adapter base in this embodiment is threaded into a dart tip having a sharpened tubular end portion for entering through skin of an animal and a cylindrical chamber portion for receiving and holding at least part of a tissue sample. The chamber portion of the dart tip has a proximal portion adapted to be removably fastened to the distal threaded end of the adapter base and a distal portion merging with the sharpened tubular end portion. The dart tip is configured to hold and retain the tissue sample within the chamber portion while the dart tip is withdrawn from the animal. The sharpened tubular end portion has two V shaped ends. These V shaped ends may converge at different angles. The dart may have at least two spaced barbs spaced symmetrically around the interior of the chamber portion. The tubular end portion in an exemplary embodiment terminates in two V shaped cuts at least one of which is at an angle of about 30° to a longitudinal axis through the dart.

These and other embodiments in accordance with the present disclosure will become more apparent upon a reading and understanding of the following detailed description of various embodiments when taken in conjunction with the drawings.

DETAILED DESCRIPTION

Figure 1:
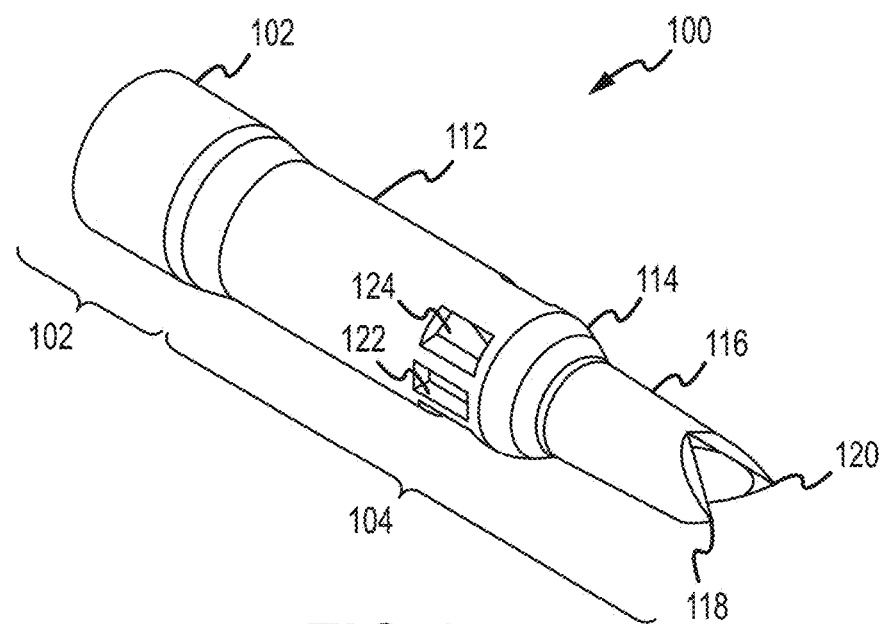
FIG. 1 is a perspective view of an exemplary dart tip in accordance with the present disclosure.

A biopsy dart 100 in accordance with the present disclosure, hereafter called a "TissueGrab biopsy dart", is designed to collect minimally invasive tissue samples from an animal such as marine mammals, fishes and sharks safely and effectively; whether subjects are sampled in the water or on-board vessels.

Each fusiform shaped TissueGrab biopsy dart 100 is composed of two pieces, a proximal (or anterior) sampling tip end 104 and the distal (or posterior) adapter base end 102. The tapered and sharpened TissueGrab tip 104 is used to define, pierce, acquire, "grab" and hold the tissue sample. The TissueGrab adapter base 102 and a chamber part of the tip 104 is used to contain the tissue sample held in the TissueGrab tip 104, and to mate the TissueGrab biopsy dart 100 to the striking device such as an arrow, pneumatic gun projectile or spear shaft used to drive or propel the biopsy dart into the flesh or blubber of the intended test subject.

Features of the TissueGrab biopsy dart 100 include the following:

The tapered, sharpened tip 118, 120 is designed to puncture and cut the subject's hide/skin in a circular pattern that defines the cylindrical shape of the sample;

The longitudinal axis of the TissueGrab 100 strikes and enters epidermal tissue of the subject preferably at a perpendicular angle;

The tip's tapered tunnel 116 compresses and advances the tissue sample as it travels from the tip, into the tunnel or tubular portion 116 and then into the expanding sample chamber (or vault) 112 as the biopsy dart 100 is being driven into the animal's flesh;

At the juncture between the tip's tapered tunnel and expanded sample chamber, there is a circular collar 114 equipped with equally spaced rectangular, recessed, partially open, backwards (distally) facing tines or barbs (angled, for example, approximately 40° to 20°) that "grab and hold" the tissue sample, preventing sample loss during retraction of the TissueGrab from the animals flesh (i.e., prevents samples from backing or reversing out);

Recessed, rectangular openings 122 equally spaced around the circular collar 114 also provide pressure release in the chamber 112 of the dart 100 while the TissueGrab dart 100 is being driven into the animal, and enables a quick visual confirmation of sample acquisition after the Tissue-Grab dart 100 has been removed from the animal;

The tip's chamber section 112 allows the tissue sample to expand as it exits the tunnel, physically preventing sample loss during retraction of the TissueGrab from the animals flesh;

Rough texturing of the interior of the chamber 112 provides a third means of ensuring that the tissue sample is not lost during extraction of the TissueGrab biopsy dart from the animal;

The female threaded rear end of the chamber portion 112 is mounted to the male threading of the adaptor base 102 during manufacturing, eliminating the need to assemble the tips 104 in the field and to specifically minimize or prevent sample contamination;

Samples can be extracted from the chamber 112 by unscrewing the adaptor base 102; and The female threading on the adapter base 102 is easily mounted to the end of a tethered pole, harpoon, crossbow or other striking device using a universal M8 hex bolt.

Every TissueGrab biopsy dart 100 comes pre-assembled, sterilized and packaged under sterile conditions.

A TissueGrab biopsy dart 100 is preferably delivered to a subject animal by mounting it to the end of a tethered pole, harpoon, crossbow arrow, or other striking device. The dart strikes its subject at approximately a perpendicular angle and enters the target subject body while gathering within it a tissue sample of approximately 1 cm$^3$.

Figure 2:
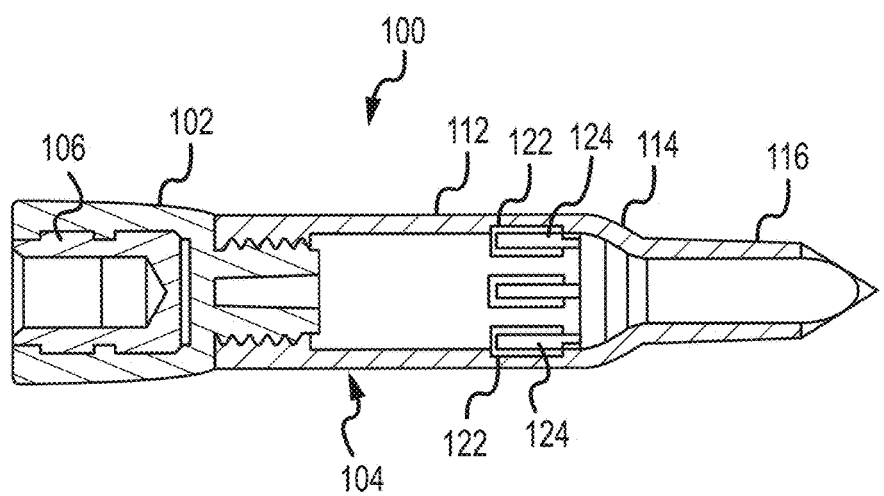
FIG. 2 is a longitudinal cross sectional view of the dart tip shown in FIG. 1.
Figure 3:
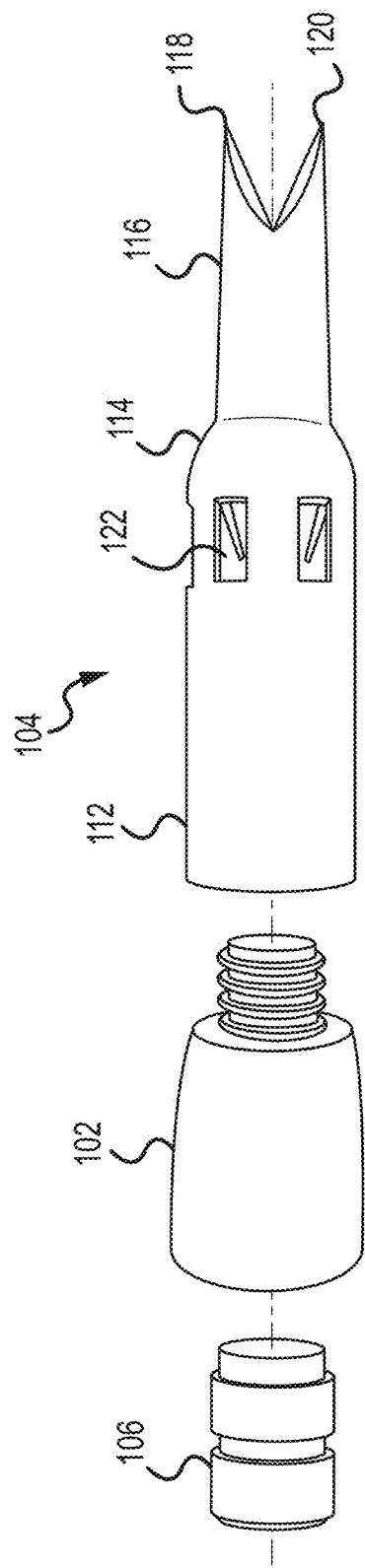
FIG. 3 is an exploded view of the exemplary dart tip shown in FIG. 1.

Turning now to the drawing figures, a perspective view of an exemplary two piece TissueGrab biopsy dart 100 is shown in FIG. 1. A longitudinal cross sectional view of the dart 100 is shown in FIG. 2. An exploded side view of an exemplary embodiment of the dart 100 is shown in FIG. 3. The biopsy dart 100 shown in FIG. 1 includes an adapter base 102 and a dart tip 104. The adapter base 102 includes a metal insert 106 that has internal female threads 108 to receive a threaded end of a shaft (not shown) such as a conventional harpoon or cross bow arrow. In the illustrated embodiment 100, the insert 106 frictionally fits within the rear of the adapter base 102.

Figure 4:
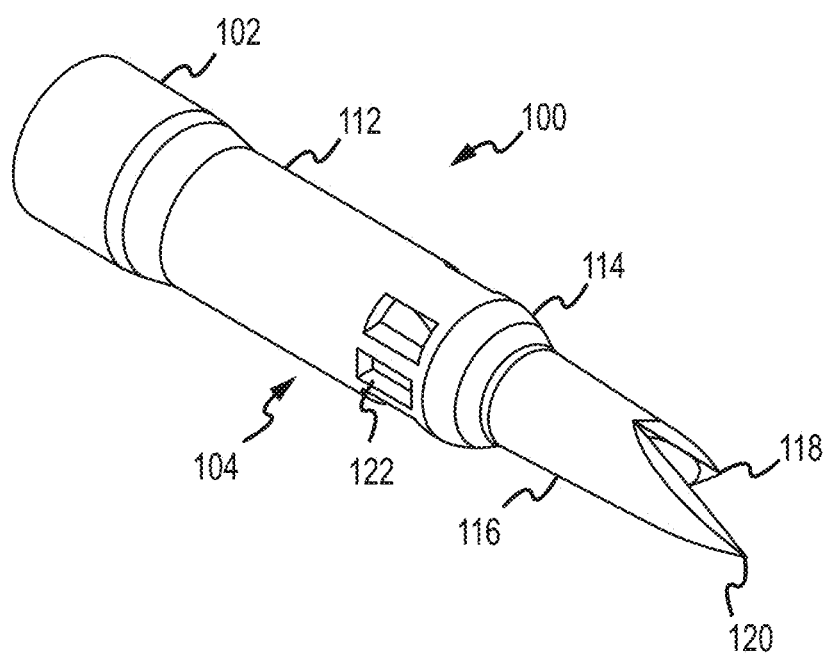
FIG. 4 is a perspective view as in FIG. 1 with an alternative tip angle configuration.

The adapter base 102 has a male threaded distal end 110 that is threaded into a proximal end portion of a hollow chamber portion 112 of the dart tip 104. The hollow chamber portion 112 of the dart tip merges via a collar 114 into a tubular end portion 116. The tubular end portion 116 is preferably a tapered cylindrical tube having a tapered cross section and has two opposite V shaped cut end points 118 and 120 formed by angle cuts through the tubular end portion 116 to form the end points. Alternatively the tubular end portion 116 may have a constant outer diameter. The V shaped cut end points 118 and 120 may be equally located axially if they are equally angularly cut, or may be axially spaced if the angles forming the V shaped cuts are different. For example, if the cuts are made at equal angles, such as 30°, the end points 118 and 120 will be spaced apart axially identical. If one half cut is at about 30° and the other half cut at about 45°, then the end points 118 and 120 would be offset axially, as is shown in FIG. 4.

The hollow chamber portion 112 preferably has an internal diameter larger than the internal diameter of the tubular end portion 116, and one or more openings 122 through the side wall of the chamber portion 112 to permit air to pass out of the dart 100 as the dart 100 is driven through the skin into the flesh of a target animal. The hollow chamber portion 112 also has a plurality of barbs 124 formed by the wall of the chamber portion 112 adjacent the collar 114 between the chamber portion 112 and the tubular end portion 116. These barbs 124 angle or project inward into the chamber portion 112 toward the adapter base 102 so as to permit tissue entry and prevent tissue withdrawal, i.e. grab and hold the tissue captured within the chamber portion 112 of the dart tip 104 as the dart 100 is retrieved from the animal being sampled. In the illustrated embodiment 100, there are six equally spaced barbs 124 spaced around the collar 114 of the chamber portion 112. Other embodiments are envisioned with from 2 to 6 barbs to achieve this functionality.

The dart 100 may be made entirely of metal, for example, stainless steel. In such an embodiment, there would be no need for an insert 106. The adapter base 102 would simply have a rear end configured to receive the shaft (not shown) of a cross bow arrow, spear, harpoon or other striking device. The front end of the adapter base 102 would include male threads sized to engage complementary threads in the chamber portion 112 of the dart tip 104.

In the embodiment 100 shown, however, the adapter base 102 and dart tip 104 are both made of a polymeric material such as nylon, glass filled nylon, carbon fiber composite or other structural composite material having sufficient rigidity to accommodate the shock and stresses involved in deployment of the dart 100. As such the wall thickness of the chamber portion 112 and the adapter base 102 is somewhat greater than their metal counterparts would be.

Once the dart 100 is retrieved from a target animal the adapter base 102 is removed from the arrow shaft and the dart tip 104 is removed via unscrewing it from the adapter base 102. The sample may then be pushed further through the chamber portion 112 and extracted from the dart tip 104 for analysis. Then a new dart 100 is installed onto an appropriate shaft for a next sample grab, thus minimizing potential cross-contamination between samples.

The biopsy dart 100 in accordance with the present disclosure may be constructed from a variety of materials including aluminum or stainless steel, a polymer such as Acetal, thermoplastic elastomer, ABS, HDPE, polycarbonate, glass filled nylon, and medical grade nylon. This range of materials enables material properties to be tailored to specific biological, biophysical and biochemical sampling applications. Where an adapter base insert 106 is needed, a suitable material is preferably brass. In such an embodiment, the external surface of the insert 106 could be knurled or roughened and thermally bonded/welded into the adapter base 102.

As illustrated, the biopsy dart 100 inner diameter tubular portion 116 is approximately about 6 mm with the chamber inner diameter being approximately 8 mm. This permits some tissue expansion as the tissue enters the chamber portion 112.

There are many alternatives and modifications that will be apparent to those skilled in the art. For example, the dart 100 may be configured with additional sharp points 118 and 120 created by additional cuts to form the additional points. Alternatively a single conical circular cut may be used on the distal end of the tubular portion 116 instead of points. The cylindrical chamber portion 112 may be configured with a plurality of axially extending slots in the side wall of the chamber portion 112 rather than the rectangular openings 122 as illustrated. The tubular portion 116 may include one or more internally directed barbs to inhibit tissue sample withdrawal through the tip in the event that the dart 100 does not enter into a target animal's body enough to draw tissue into the chamber portion 112. All such changes, alternatives and equivalents in accordance with the features and benefits described herein, are within the scope of the present disclosure. Such changes and alternatives may be introduced without departing from the spirit and broad scope of my invention as defined by the claims below and their equivalents.

What is claimed is:

1. A dart for use in gathering a biological tissue sample from a marine animal, the dart comprising:
   an adapter base for fastening to an elongated dart delivery shaft or striking device;
   a dart tip having a sharpened tubular end portion for entering through skin of a marine animal, when the dart tip is driven into the marine animal from a distance via the delivery shaft or striking device, and a chamber portion having an internal transverse cross-sectional diameter larger than an internal transverse cross-sectional diameter of the tubular end portion for collecting and holding a tissue sample, wherein the chamber portion has a proximal portion adapted to be fastened to the adapter base and a distal portion merging with the tubular end portion via a tapered collar portion and one or more openings through a side wall of the chamber portion; and
   one or more barbs formed in the chamber portion for preventing withdrawal of the tissue sample through the sharpened tubular end portion while the dart tip is withdrawn from the live marine animal.

2. The dart according to claim 1 wherein the one or more barbs project inward and toward the adapter base.

3. The dart according to claim 1 wherein the sharpened tubular end portion has two V shaped end points.

4. The dart according to claim 3 wherein the V shaped end points are at different axial locations.

5. The dart according to claim 1 wherein there are six spaced barbs spaced symmetrically around a collar of the chamber portion.

6. The dart according to claim 1 wherein the tubular end portion terminates in two V shaped cuts each at an angle of about 30° to a longitudinal axis through the dart.

7. The dart according to claim 1 wherein a distal end portion of the chamber portion is externally tapered.

8. A dart for use in gathering a biological tissue sample from a marine animal comprising:
   a generally cylindrical adapter base for fastening to a dart delivery shaft or striking device, the adapter base having a distal threaded end;
   a dart tip having a sharpened tubular end portion for entering through skin of a marine animal, when the dart tip is driven into the marine animal from a distance via the delivery shaft or striking device, and a chamber portion having an internal transverse cross-sectional diameter larger than an internal transverse cross-sectional diameter of the tubular end portion for collecting and holding a tissue sample, wherein the chamber portion has a proximal portion adapted to be fastened to the distal threaded end of the adapter base and a distal portion merging with the sharpened tubular end portion via a tapered collar portion and one or more openings through a side wall of the chamber portion; and
   a plurality of barbs formed in the chamber portion for preventing withdrawal of the tissue sample through the sharpened tubular end portion while the dart tip is withdrawn from the animal.

9. The dart according to claim 8 wherein the plurality of barbs project inward and toward the adapter base.

10. The dart according to claim 8 wherein the sharpened tubular end portion has two V shaped end points.

11. The dart according to claim 10 wherein the V shaped end points are at different angles.

12. The dart according to claim 8 wherein there are six barbs spaced symmetrically around a collar of the chamber portion.

13. The dart according to claim 8 wherein the tubular end portion terminates in two V shaped cuts at least one of which is at an angle of about 30° to a longitudinal axis through the dart.

14. The dart according to claim 8 wherein a distal portion of the chamber portion is externally tapered.

15. The dart according to claim 14 wherein the tubular end portion terminates in two V shaped cuts at least one of which is at an angle of about 30° to a longitudinal axis through the dart.

16. A dart for use in gathering a biological tissue sample from a marine animal comprising:
- an adapter base for fastening to an elongated dart delivery shaft or striking device, the adapter base having a distal threaded end; and
- a dart tip having a sharpened tubular end portion for entering through skin of a marine animal, when the dart tip is driven into the marine animal from a distance via the delivery shaft or striking device, and a cylindrical chamber portion having an internal transverse cross-sectional diameter larger than an internal transverse cross-sectional diameter of the tubular end portion for receiving and holding at least part of a tissue sample, wherein the chamber portion has a proximal portion adapted to be removably fastened to the distal threaded end of the adapter base and a distal portion merging with the sharpened tubular end portion via a tapered collar portion and one or more openings through a side wall of the chamber portion, wherein the dart tip is configured to hold and retain the tissue sample within the chamber portion while the dart tip is withdrawn from the animal.

17. The dart according to claim 16 wherein the sharpened tubular end portion has two V shaped end points.

18. The dart according to claim 17 wherein the V shaped end points converge at different angles.

19. The dart according to claim 16 wherein there are at least two spaced barbs spaced symmetrically around the chamber portion.

20. The dart according to claim 16 wherein the tubular end portion terminates in two V shaped cuts at least one of which is at an angle of about 30° to a longitudinal axis through the dart.

* * * * *